(12) United States Patent
Beise (10) Patent No.: US 7,860,560 B2
(45) Date of Patent: Dec. 28, 2010

(54) METHOD FOR EVALUATING HEART RATE VARIABILITY

(75) Inventor: Reinhard D. Beise, Ottenhofen (DE)

(73) Assignee: BioSign GmbH, Ottenhofen (DE)

( * ) Notice: Subject to any disclaimer, the term of this patent is extended or adjusted under 35 U.S.C. 154(b) by 658 days.

(21) Appl. No.: 11/894,161

(22) Filed: Aug. 20, 2007

(65) Prior Publication Data

US 2008/0058662 A1 Mar. 6, 2008

(30) Foreign Application Priority Data

Aug. 25, 2006 (DE) .................. 10 2006 039 957

(51) Int. Cl.
*A61B 5/04* (2006.01)
(52) U.S. Cl. ...................... 600/523; 600/509
(58) Field of Classification Search ................. 600/509, 600/510, 519
See application file for complete search history.

(56) References Cited

FOREIGN PATENT DOCUMENTS

WO   WO 00/51677   9/2000

OTHER PUBLICATIONS

V.P.S. Naidu, M.R,S. Reddy, "*Autoregressive (AR) Based Power Spectral Analysis Of Heart Rate Time Series Signal (HRTS) Signal*" Biomedical Eng. Division, Indian Institute of Technology, Chennai, India. vpsnaidu_nal@yahoo.co.in TENCON 2003, pp. 1391-1394.

Ahuja et al., "*Heart Rate Variability and its Clinical Application for Biofeedback*" V.E.S. Institute of Technology, 17th IEEE Symposium on computer-Based Medical Systems (CBMS'04) Computer Society.

Malik et al., Task Force of the European Society of Cardiology and the North American Society of Pacing and Electrophysiology, "*Heart Rate Variability Standards of Measurement, Physiological Interpretation, and Clinical Use*" (Circulation, vol. 93, No. 5, Mar. 1, 1996; pp. 1043-1064).

*Primary Examiner*—Carl H Layno
*Assistant Examiner*—Brian T Gedeon
(74) *Attorney, Agent, or Firm*—Wolf, Greenfield & Sacks, P.C.

(57) ABSTRACT

The heartbeat frequency is not constant but subject to natural variations. This change in heartbeat frequency is called the heart rate variability (HRV). A method is provided for online-displaying a HRV biofeedback signal by which the cardiovascular state of a patient can be purposefully influenced. The parameters $HRV_i$ as determined according to the invention are used for said HRV biofeedback signal, wherein, as a function of the display, the patient should alter his behaviour in such a way that a desired cardiovascular state is attained. The inventive $HRV_i$ parameters provide a HRV biofeedback signal with high dynamics which allow the patient to react quickly to changes and therewith to reliably achieve and stabilise his own desired cardiovascular state.

7 Claims, 13 Drawing Sheets

METHOD FOR EVALUATING HEART RATE VARIABILITY

The invention relates to a method for evaluating a plurality of sampling sequences $f_{h,i}(kT_s)$ where i=1, 2, 3, . . . , m and k=0, 1, 2, . . . , n, wherein each sampling sequence $f_{h,i}(kT_s)$ represents the sampling sequence of the heart rate $f_h$ of a patient over the period n·$T_s$.

The heartbeat frequency ($f_h$) is not constant but subject to natural variations. This change in heartbeat frequency is called the heart rate variability (HRV). To determine the HRV the heartbeats supplied per unit of time by an electrocardiograph (ECG) or a pulse sensor are usually interpolated for a predefined sampling period ($T_s$), so there is a heart rate value for each multiple of the sampling period. The sampling period can for example be $T_s$=0.1 s, the corresponding sampling frequency ($f_s$) is then $f_s$=10 Hz. A large number of calculation and evaluation methods are known for the HRV on the basis of this sampling sequence of the heart rate $f_h(kT_s)$ where k=0, 1, 2, . . . . Some of these calculation and evaluation methods are described in "Heart Rate Variability: Standards of Measurement, Physiological Interpretation and Clinical Use, Task Force of the European Society of Cardiology and the North American Society of Pacing and Electrophysiology, Circulation, Vol. 93 No. 5, Mar. 1, 1996".

The aim of any HRV calculation method is to make certain statements about the manner in which the HRV is affected by certain physical states.

In general it can be stated that the HRV is a measure of the body's ability to adapt to internal and external stresses and is substantially influenced by variations in the cardiovascular state. Conversely attempts are therefore made to use certain HRV parameters as indicators of specific cardiovascular states. The cardiovascular state is in turn decisively controlled by the two components of the vegetative nervous system, the sympathicus and the parasympathicus. The sympathicus controls the internal organs in such a way that in the event of extraordinary exertions a sudden increase in the body's performance can be attained whereas the parasympathicus, as an opponent to the sympathicus, is used for metabolism, regeneration and building up the body's own reserves.

In states of rest and relaxation the HRV is characterized for example in that the heart rate increases and decreases again in a very regular rhythm, and, more precisely, about 6 times per minute. A very pronounced maximum frequency can be detected at about 0.1 Hz with a spectral analysis of a sampling sequence of the heart rate $f_h(kT_s)$ corresponding to this state. This relatively stable cardiac rhythm can be explained by the fact that the heart rate changes directly with the respiratory rate in this case. During inhalation the heart rate accordingly increases owing to the increased venous backflow, whereas it decreases again during exhalation. This state is called Respiratory Sinus Arrhythmia (RSA) (Sinus Arrhythmia is generally designated as the irregular heartbeat sequence as a consequence of irregular stimulation in the sinu-auricular nodes).

In addition to the RSA state (i.e. as a rule in the case of stress) HRV is, by contrast, identified by a broad spectrum of frequency fractions between 0 . . . 0.8 Hz, wherein the average power density of this spectrum decreases as the frequency increases.

It is also known to purposefully influence the cardiovascular state of a patient using what are known as biofeedback methods. In these methods a suitable physical signal (i.e. for example an HRV parameter or the electrical skin resistance) is measured and shown to the patient, wherein, as a function of the displayed value, the patient should alter his behavior in such a way that a desired cardiovascular state is attained.

With HRV biofeedback an HRV parameter is therefore determined online and shown to the patient in a suitable manner by way of processing. The aim is to supply the patient with an HRV biofeedback signal which allows a statement to be made about whether his body currently finds itself in a desired cardiovascular state or not. If the HRV biofeedback signal indicates a difference in the desired cardiovascular state, the patient can adapt his behavior accordingly to return to the desired cardiovascular state. The HRV biofeedback method can for example therefore be used to purposefully put the patient into an RSA state. It is assumed in this connection that the RSA state can contribute to some of the body's own regulatory processes being able to take place more efficiently again, so the RSA state can be helpful primarily in treating patients with psychosomatic disorders.

Basically various HRV parameters are known from the prior art which are each intended to be usable as an indicator of the RSA state. The term "Entrainment Mode" is often used in this connection in the prior art as a common name for the RSA state.

WO 00/051677 A2 describes a method and a device for determining an HRV parameter from a frequency distribution of a given sampling sequence of the heart rate $f_h(kT_s)$ determined by way of Fourier transform. The HRV parameter should, moreover, provide a statement as to whether the patient is in the RSA state or not. The RSA state should in turn be attained if the patient's HRV passes from a broad frequency distribution with average amplitude to a narrow frequency distribution with high amplitude.

It is also known from "Heart Rate Variability: Standards of Measurement, Physiological Interpretation and Clinical Use, Task Force of the European Society of Cardiology and the North American Society of Pacing and Electrophysiology, Circulation, Vol. 93 No. 5, Mar. 1, 1996" to analyse the frequency distribution of the HRV with a power ratio LF/HF, wherein LF is the power of the HRV in the frequency range 0.04-0.15 Hz and HF the power of the HRV in the frequency range 0.15-0.4 Hz.

Overall however it has been found that the HRV parameters known from the prior art are not optimally suitable as HRV biofeedback signals for achieving the RSA state. Until now no parameter has been found which reliably allows the patient to achieve the RSA state by changing his respiratory frequency via HRV biofeedback.

It is therefore the object of the invention to provide a parameter of HRV which allows a patient to reliably stabilize his own RSA state by means of HRV biofeedback. This object is achieved by a method according to claim 1.

The solution according to the invention is based on a targeted modification of the power ratio LF/HF known from the prior art. It has been acknowledged as a problem of the power ratio LF/HF that this power ratio supplies inadequate dynamics as an HRV biofeedback signal, i.e. the maximum and minimum values of the HRV biofeedback signal vary as a function of the cardiovascular states of the patient (including the RSA state) by an insufficient factor. In contrast, the invention provides HRV biofeedback signals with higher dynamics which allow the patient to react quickly to changes in the biofeedback signal and therewith to better stabilize the RSA state.

For each sampling sequence $f_{h,i}(kT_s)$ the method according to the invention comprises the following steps:

Determining a distribution function $F_{h,i}(f)$ for each sampling sequence $f_{h,i}(kT_s)$ as a function of the frequency, Determining a first integral fraction $I_{max,i}$ of the distribution function $F_{h,i}(f)$ for a first frequency range, wherein the first frequency range includes a maximum of the distribution function $F_{h,i}(f)$, Determining a second integral fraction $I_{ref,i}$ of the distribution function $F_{h,i}(f)$ for a second frequency range which includes additional or different frequency ranges to the first frequency range, Standardizing the integral fractions $I_{max,i}$ and $I_{ref,i}$ using a standardizing factor $K_{ref}$ where $$\tilde{I}_{max,i} = K_{ref} * I_{max,i}$$

and $$\tilde{I}_{ref,i} = K_{ref} * I_{ref,i}$$

in such a way that for the second integral fraction the condition $\tilde{I}_{ref,i} \geq 1$ is satisfied, Determining a parameter $HRV_i$ for each sampling sequence $f_{h,i}(kT_s)$ with the respective integral fractions $\tilde{I}_{max,i}$ and $\tilde{I}_{ref,i}$ with a function $f(\tilde{I}_{ref})$ according to $$HRV_i = \tilde{I}_{max,i} * f(\tilde{I}_{ref,i}),$$

wherein the function $f(\tilde{I}_{ref})$ for each integral fraction $\tilde{I}_{ref,i}$ satisfies the conditions $$1 > f(\tilde{I}_{ref,i}) > \frac{1}{\tilde{I}_{ref,i}}$$

and $$0 > \left.\frac{\partial f(\tilde{I}_{ref})}{\partial \tilde{I}_{ref}}\right|_{\tilde{I}_{ref,i}} > -\frac{f(\tilde{I}_{ref,i})}{\tilde{I}_{ref,i}}$$

and wherein the function $f(\tilde{I}_{ref})$, the first and second frequency ranges and the standardizing factor $K_{ref}$ are the same for all m evaluated sampling sequences $f_{h,i}(kT_s)$.

The integral fraction $\tilde{I}_{max}$ represents the LF fraction known from the prior art whereas the integral fraction $\tilde{I}_{ref}$ corresponds to the HF fraction known from the prior art.

The increase in the dynamics of the HRV biofeedback signal is achieved according to the invention in that with the power ratio LF/HF known from the prior art, the HF fraction is weighted more strongly. This measure is in turn based on the recognition that the LF fraction and the HF fraction affect the indicator effect differently with respect to the RSA state. In particular the following connections between the LF fraction and the HF fraction on the one hand and the resulting indicator effect have been found in numerous patient tests:

1. Probability of the Occurrence of an RSA State

Figure 1:
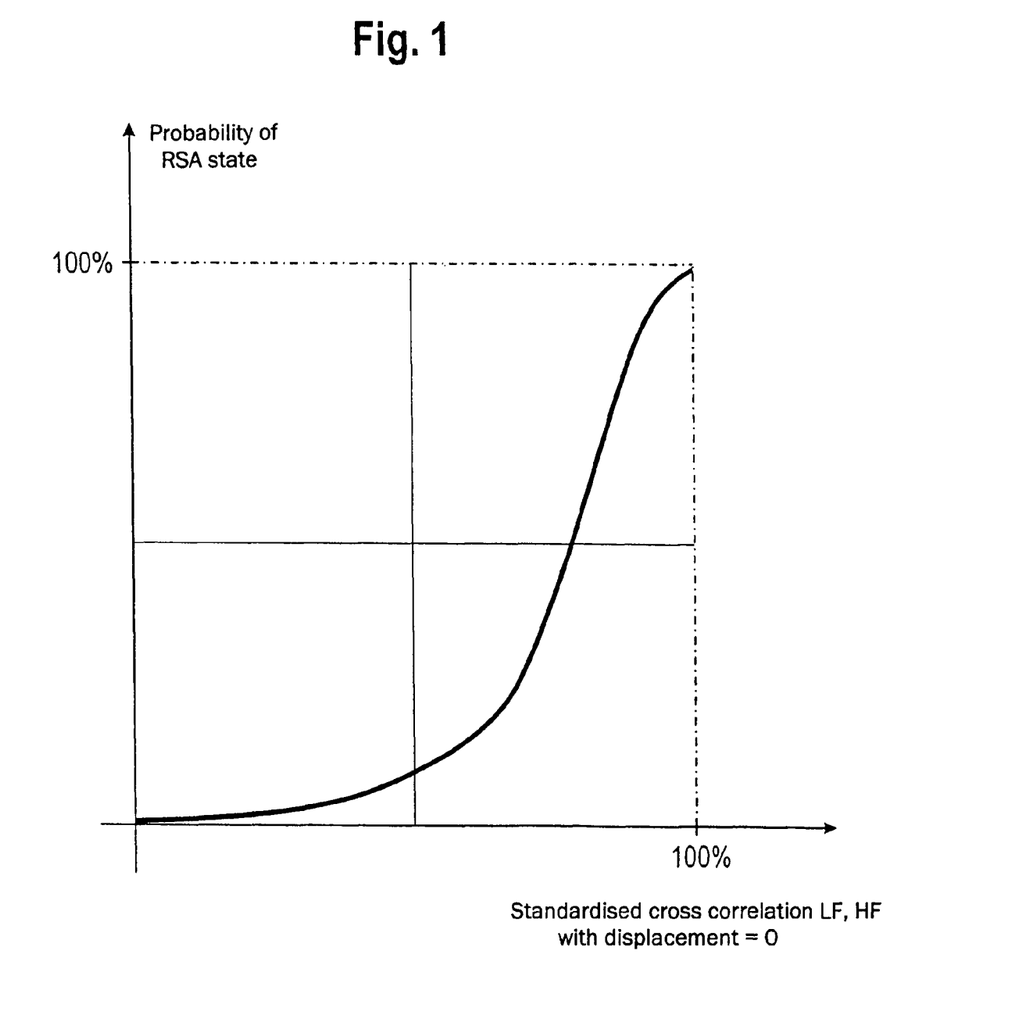
FIG. 1 shows the connection found between the standardized cross correlation of the LF fraction and the HF fraction with a displacement 0 and the occurrence of the RSA state.

FIG. 1 shows the connection found between the standardized cross correlation of the LF fraction and the HF fraction with a displacement 0 and the occurrence of the RSA state. A value of 100% on the abscissa corresponds to the normal product of the two autocorrelations of the LF fraction and HF fraction for the displacement 0. If, therefore, the characteristics of the LF fraction and the HF fraction correlate strongly over time then there is a high probability that an RSA state has occurred. This connection is independent of the actual values of the LF fraction and HF fraction, which is why the ratio LF/HF provides a more or less calibrated parameter of HRV on the basis of this connection. Variations in the value of the LF fraction and HF fraction can thus be effectively compensated.

2. Indicator Effect of LF/HF as a Function of the LF Fraction

Figure 2:
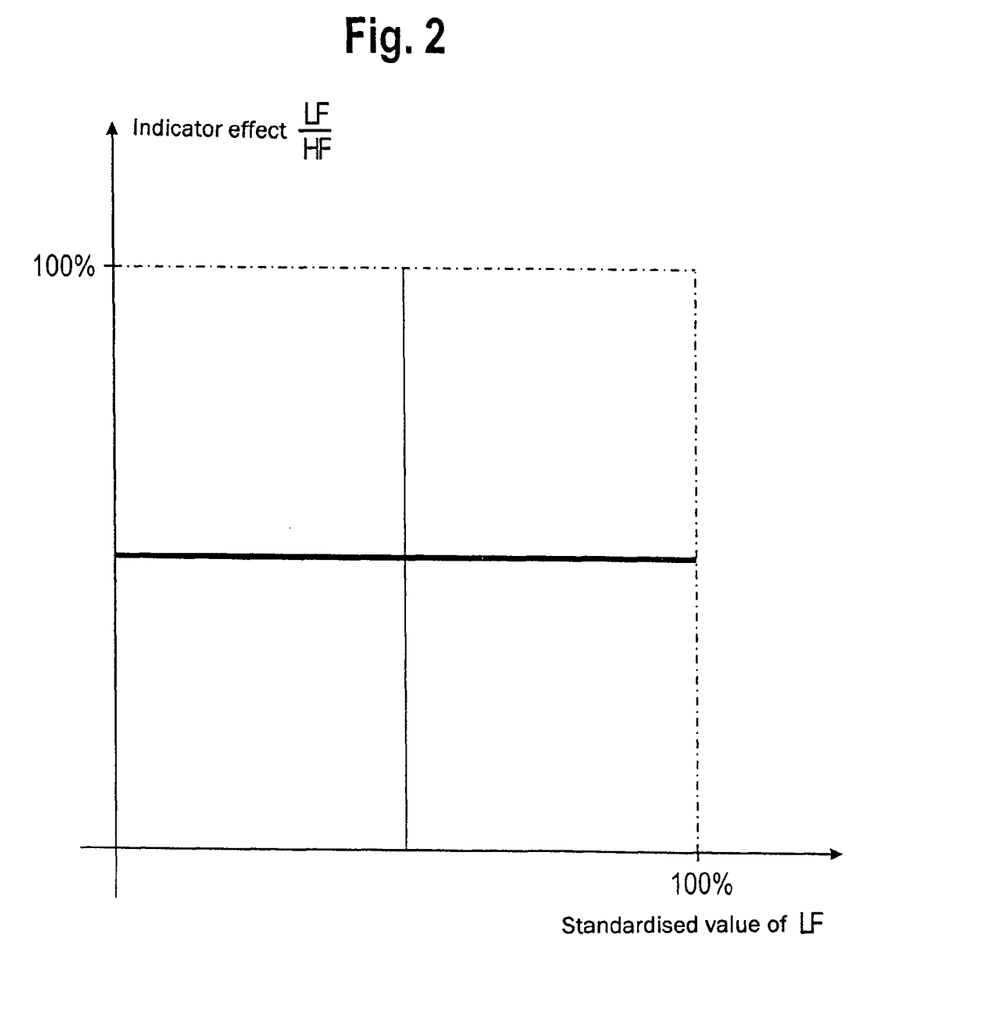
FIG. 2 shows the connection found between the standardized value of the LF fraction and the indicator effect of the ratio LF/HF with respect to the RSA state.

FIG. 2 shows the correlation found between the standardized value of the LF fraction and the indicator effect of the ratio LF/HF with respect to the RSA state. It has been found that changes in the value of the LF fraction have almost no effect on the indicator effect with respect to the ratio LF/HF.

3. Indicator Effect LF/HF as a Function of the HF Fraction

Figure 3:
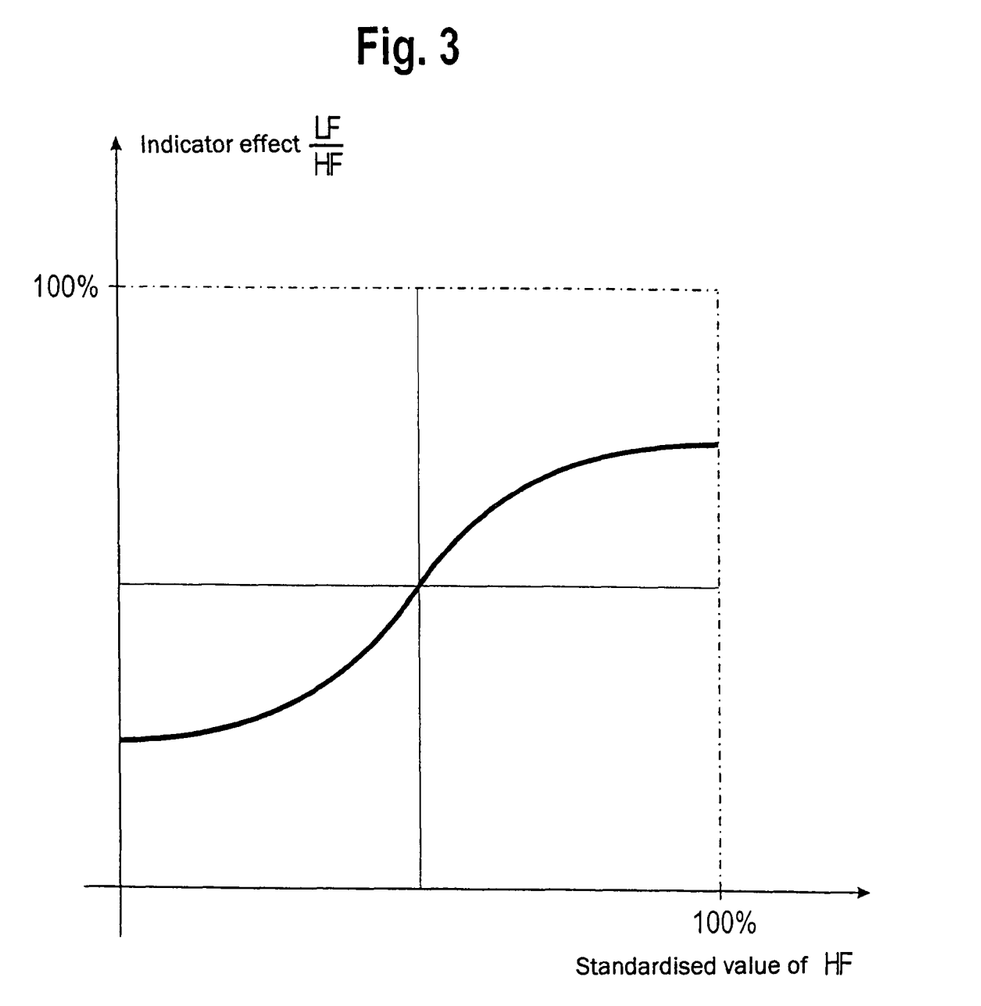
FIG. 3 shows the connection found between the standardized value of the HF fraction and the indicator effect of the ratio LF/HF with respect to the RSA state, FIG. 4 show the connection found between the standardized value of the LF fraction and the indicator effect of the LF fraction with respect to the RSA state.

FIG. 3 shows the connection found between the standardized value of the HF fraction and the indicator effect of the ratio LF/HF with respect to the RSA state. It has been found that, in contrast to the LF fraction, changes in the value of the HF fraction have a marked impact on the indicator effect of the ratio LF/HF. Moreover it emerges from the correlation found according to FIG. 3 that HF fractions with high values provide a more reliable HRV parameter than HF fractions with low values on the basis of the ratio LF/HF.

4. Indicator Effect of LF as a Function of the LF Fraction

Figure 4:
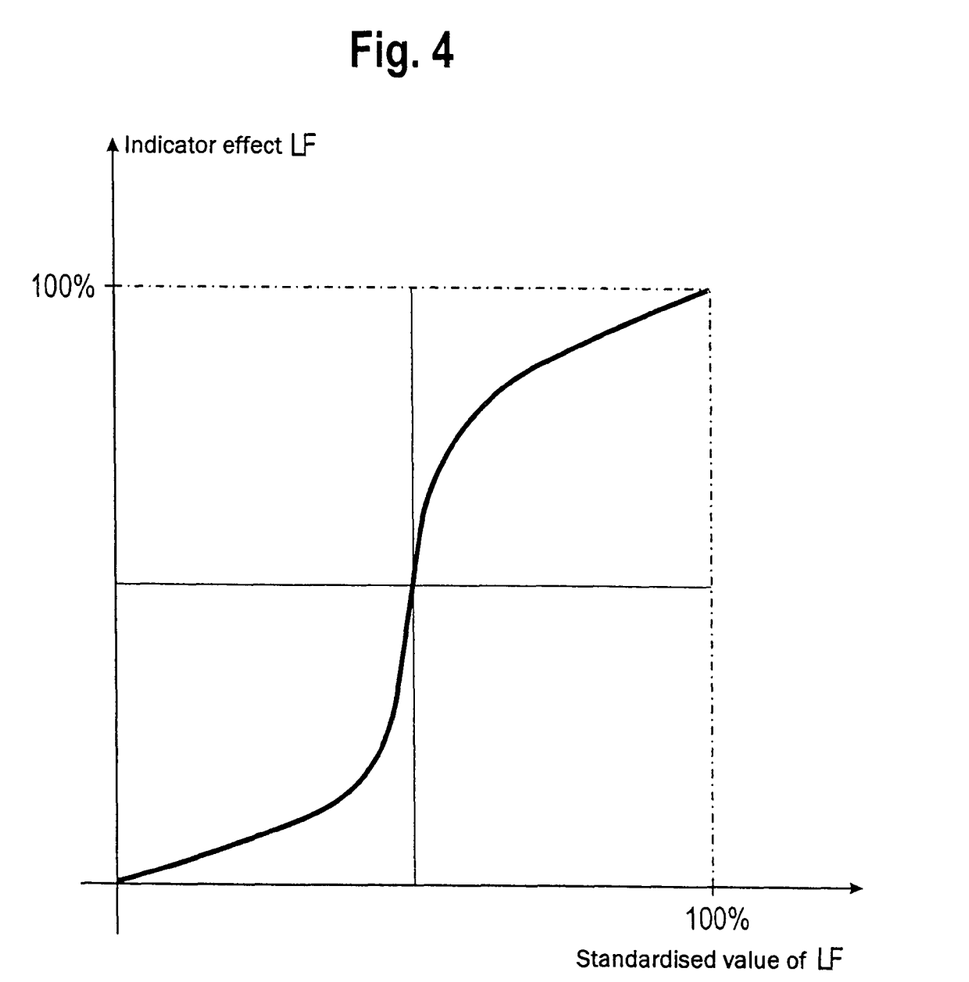

Finally, FIG. 4 shows the connection found between the standardized value of the LF fraction and the indicator effect of the LF fraction with respect to the RSA state. In this case only the LF fraction is used as a HRV parameter. It has been found that the probability of an RSA state increases as the value of the LF fraction increases. At the same time however it must be observed that the LF fraction often has great fluctuations in value with great variance, and this is not obvious from FIG. 4. However, this means that the LF fraction does not provide a standardized HRV parameter and is therefore not suitable as an exclusive parameter for biofeedback methods.

The connections according to FIGS. 1 to 4 may be summarized as follows:

The ratio LF/HF is suitable as an HRV parameter for recognizing the RSA state primarily because variations in the values of the LF fraction and HF fraction are effectively compensated. A more or less calibrated value is thus produced, of which the amount is largely independent of the measuring conditions (such as internal multiplication factors, the choice of evaluation method, etc.).

As an HRV parameter the sole LF fraction provides significantly better dynamics than the ratio LF/HF for recognizing the RSA state, although there is again the problem of calibrating the value in this case. A specific value (i.e. for example the value 100) can then have a completely different indicator effect from device to device, so each device must first of all be individually calibrated by the patient.

High values of the HF fraction are more significant than low values with respect to the indicator effect of the ratio LF/HF.

Figure 5:
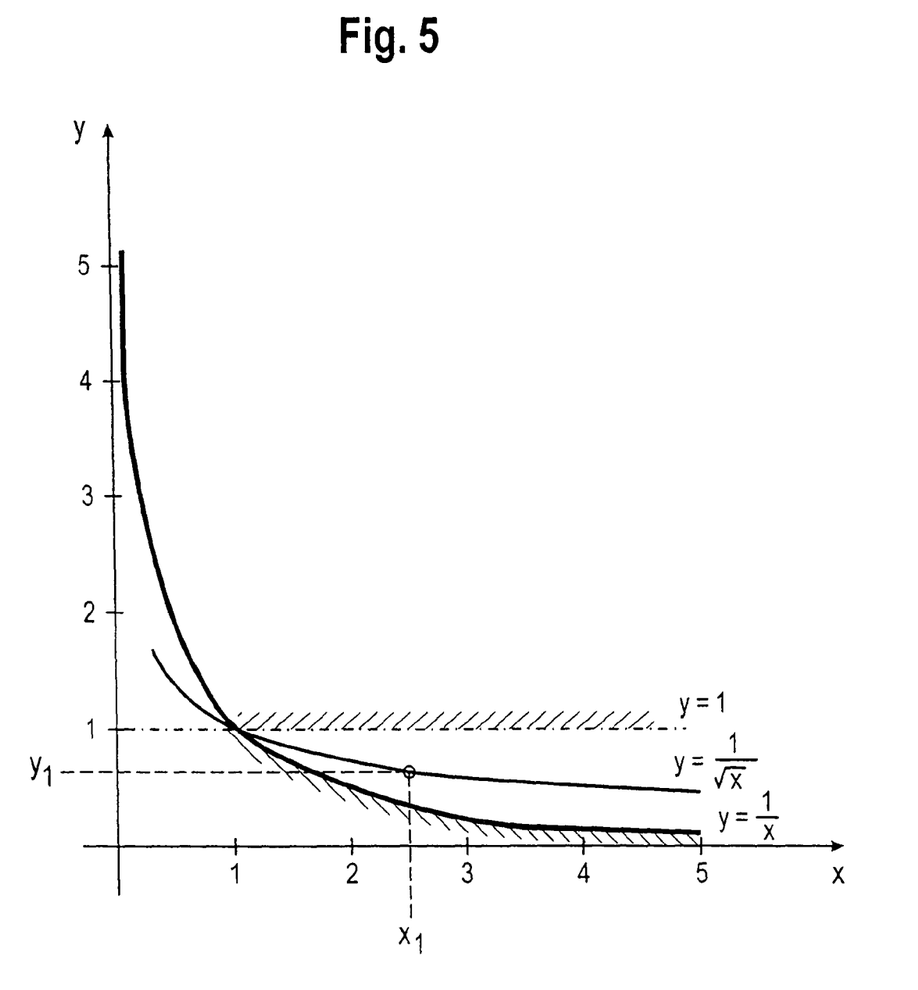
FIG. 5 shows an X-Y coordinate system with the functions $y=1/x$, $y=1/\sqrt{x}$ and $y=1$.

The invention optimizes these connections and finds a more or less optimal compromise between the good dynamics of the LF fraction and the reliable calibrating function of the LF/HF ratio. According to the invention the integral fraction $\tilde{I}_{max}$ is therefore not multiplied by the reciprocal value $1/\tilde{I}_{ref}$ but by the function $f(\tilde{I}_{ref})$, wherein the function $f(\tilde{I}_{ref})$ is subjected to certain boundary conditions to attain said compromise. To illustrate these boundary conditions FIG. 5 shows an X-Y coordinate system with the functions $y=1/x$, $y=1/\sqrt{x}$ and $y=1$. The standardizing factor $K_{ref}$ is selected for all $\tilde{I}_{ref,i}$ such that $\tilde{I}_{ref,i} \geq 1$ is satisfied. In addition, according to the invention the value condition $$1 > f(\tilde{I}_{ref,i}) > \frac{1}{\tilde{I}_{ref,i}},$$

applies, so all possible functions $f(\tilde{I}_{ref})$ have to assume values in the hatched area which is delimited by y=1 and y=1/x. In this area the function $f(\tilde{I}_{ref})$ should, moreover, be selected such that the gradient condition $$0 > \frac{\partial f(\tilde{I}_{ref})}{\partial \tilde{I}_{ref}}\bigg|_{\tilde{I}_{ref,i}} > -\frac{f(\tilde{I}_{ref,i})}{\tilde{I}_{ref,i}}$$

is also satisfied. This condition states that the gradient of function $f(\tilde{I}_{ref})$ should always be flatter than the gradient of the corresponding function $y=K_s \cdot 1/x$ which would run through the point $(\tilde{I}_{ref,i}, f(\tilde{I}_{ref,i}))$. $K_s$ is the corresponding extension factor for the function $1/x$.

The gradient condition shall be illustrated in more detail using the function $y=1/\sqrt{x}$: for $x>1$ the function $y=1/\sqrt{x}$ first of all assumes only the function values in the hatched area, so the first condition is satisfied. The gradient condition at point $(x_1,y_1)$ accordingly states that the gradient of $y=1/\sqrt{x}$ should be flatter at this point than the gradient of the function $K_s \cdot 1/x$ which would run through this point. $K_s$ assumes the value $x_1 \cdot y_1$ in this connection or, when expressed generally, $\tilde{I}_{ref,i} \cdot f(\tilde{I}_{ref,i})$. Since the derivation of the function $y=1/x$ is equal to $y'=-1/x^2$, for the point $(x_1,y_1)$ the boundary gradient is $-y_1/x_1$ or, when expressed generally, $-f(\tilde{I}_{ref,i})/\tilde{I}_{ref,i}$. The derivation of the function $y=1/\sqrt{x}$ is, moreover, $y'=-0.5 \cdot x^{-3/2}$ and therewith assumes the value $-0.5 \cdot y_1/x_1$ at point $(x_1,y_1)$. The resulting condition is therefore $-0.5 \cdot y_1/x_1 > -y_1/x_1$ or $1>0.5$, so the gradient condition is satisfied for the function $y=1/\sqrt{x}$. For the function type $y=1/x^a$ it therefore generally applies that the gradient condition is satisfied if the parameter is between 0 and 1, i.e. if $0<a<1$ is satisfied.

The gradient condition has the effect that, in relative terms, the functional fraction $f(\tilde{I}_{ref})$ is more strongly weighted than the function $1/\tilde{I}_{ref}$ for higher values of $\tilde{I}_{ref}$. The indicator effect shown in FIG. 3 is thus also more strongly weighted for high values of HF or for high values of the integral fraction $\tilde{I}_{ref}$, and, according to the invention, this then leads to greater dynamics of the parameter $HRV_i$.

Moreover it follows from the value condition that the HRV parameter $HRV_i$ always assumes higher values than the ratio LF/HF.

Both conditions together, i.e. the value condition and the gradient condition, thus mean that for the parameters $HRV_i$ greater dynamics can be attained with higher values than is possible with conventional calculation on the basis of the LF/HF ratio. Owing to the parameter $HRV_i$ it is thereby again more easily possible for a patient to recognize and attain his own RSA state using biofeedback.

According to a preferred embodiment the function $f(\tilde{I}_{ref})$ is defined as follows:

$$f(\tilde{I}_{ref}) = \frac{1}{(\tilde{I}_{ref})^a} \text{ where } 0 < \alpha < 1.$$

For $a \to 1$ the resulting function $\tilde{I}_{max} \cdot f(\tilde{I}_{ref})$ then approximates the power ratio LF/HF known from the prior art. By contrast, for $a \to 0$ the effect of the integral fraction $\tilde{I}_{ref}$ is completely neutralized, so only the effect of the integral fraction $\tilde{I}_{max}$ prevails.

Preferred values for the parameter a are 0.25, 0.5 or 0.75.

According to a further preferred embodiment the distribution function $F_{h,i}(f)$ is determined by way of a fast Fourier transform of the sampling sequence $f_{h,i}(kT_s)$. For discrete frequency values the fast Fourier transform supplies the corresponding amplitude or power components of the sampling sequence $f_{h,i}(kT_s)$, wherein the resolution of the frequency values depends on the number n of values of the sampling sequence $f_{h,i}(kT_s)$ and increases linearly with the number n.

A further possibility lies in determining the distribution function $F_{h,i}(f)$ by way of an autoregressive spectral estimate of the sampling sequence $f_{h,i}(kT_s)$. In this connection what are known as the AR parameters are first of all determined using the method of regressive adjustment calculation. The Z transform of the AR parameters then supplies a continuous spectral function of the sampling sequence $f_{h,i}(kT_s)$. The resolution of this spectral function depends on the one hand on the order of the AR parameters and on the other hand again on the number n of values of the sampling sequence $f_{h,i}(kT_s)$.

According to the invention the parameter $HRV_i$ can be used as an indicator of sampling sequences of the heart rate $f_h$ of a patient who is close to the RSA state or has attained the RSA state. Using this indicator, with an HRV biofeedback it is easily possible for the patient to attain the RSA state by targeted control of his own breathing.

The invention will be described in more detail hereinafter with reference to the accompanying drawings, in which:

FIG. 12 shows the observance of the value condition for the function $$f(\tilde{I}_{ref}) = \frac{1}{(\tilde{I}_{ref})^a}$$

according to the invention used for evaluation with the values a=0.25, a=0.5 and a=0.75 and FIG. 13 shows the observance of the gradient condition for the function $$f(\tilde{I}_{ref}) = \frac{1}{(\tilde{I}_{ref})^a}$$

according to the invention used for evaluation with the values a=0.25, a=0.5 and a=0.75.

FIGS. 1 to 5 have already been described by way of introduction.

Figure 6:
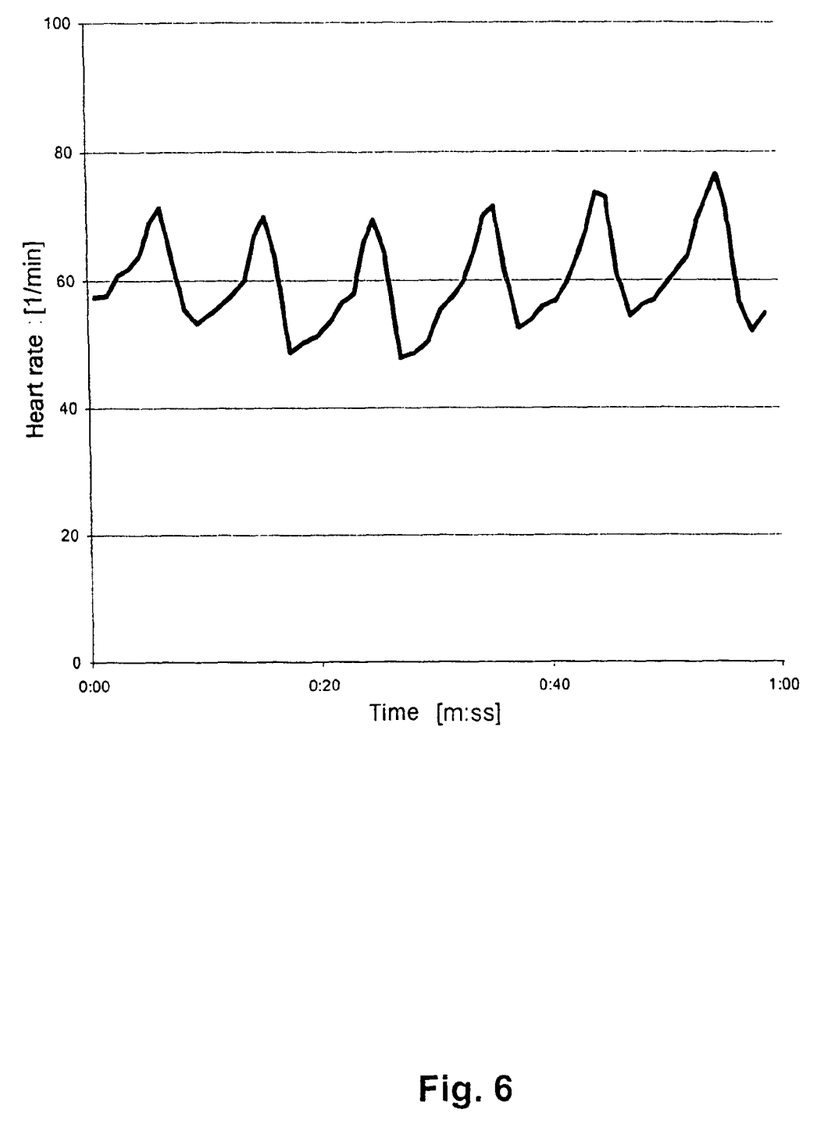
FIG. 6 shows variations in the heart rate of a patient (RSA state) caused by breathing.

FIG. 6 shows variations in the heart rate of a patient (RSA state) caused by breathing. As a result of regular and deep breathing a heart rate characteristic is established which is approximately sinusoidal. The rising sides in FIG. 1 (increase in heart rate) correspond to inhalation while the falling sides in FIG. 1 (reduction in heart rate) correspond to exhalation.

Figure 7:
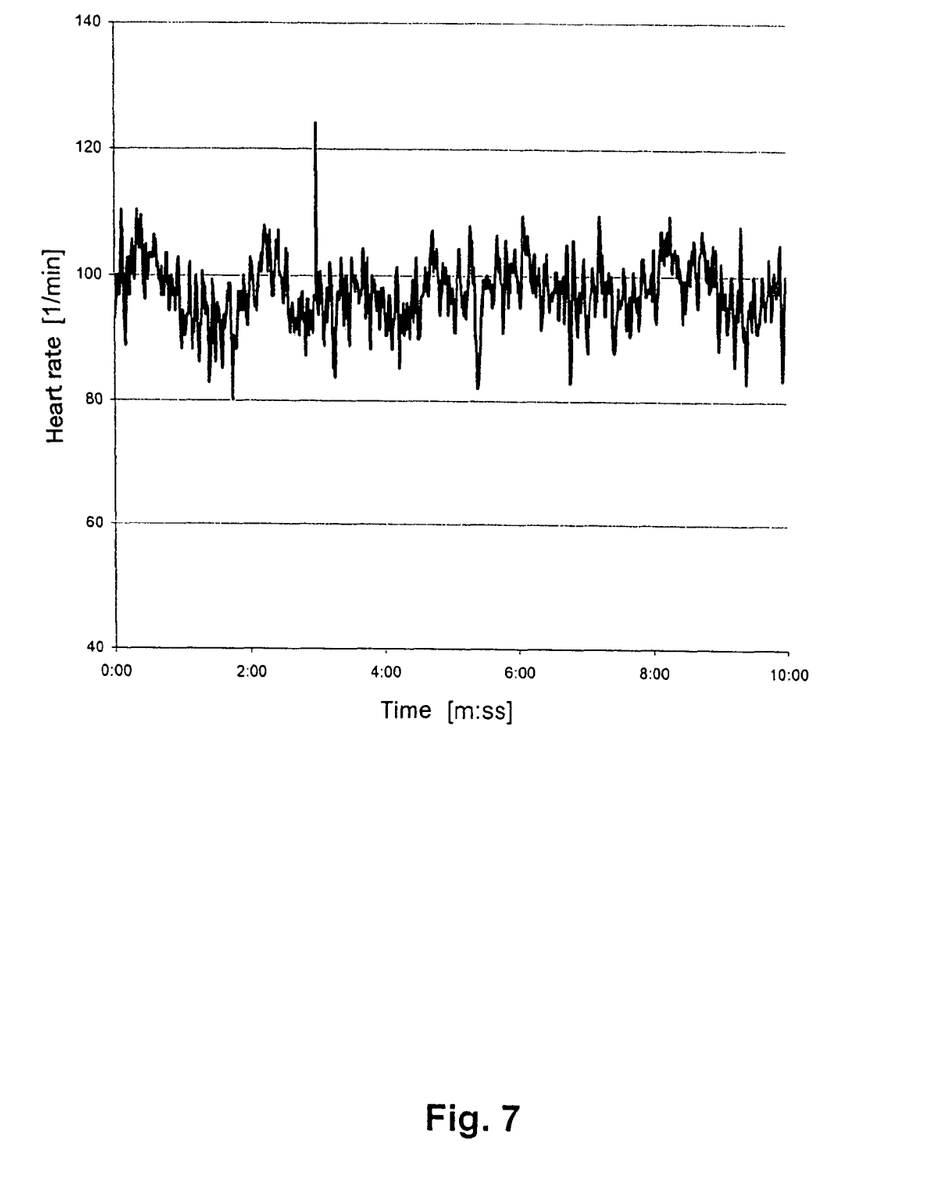
FIG. 7 shows variations in heart rate of a patient (no RSA state) caused by different regulatory processes.

FIG. 7 shows variations in the heart rate of a patient (no RSA state) caused by various regulatory processes. In this case the effect of breathing on the heart rate can no longer be discerned.

FIGS. 8 to 11 relate to the evaluation of patient measuring results which were obtained during a biofeedback session.

Figure 8:
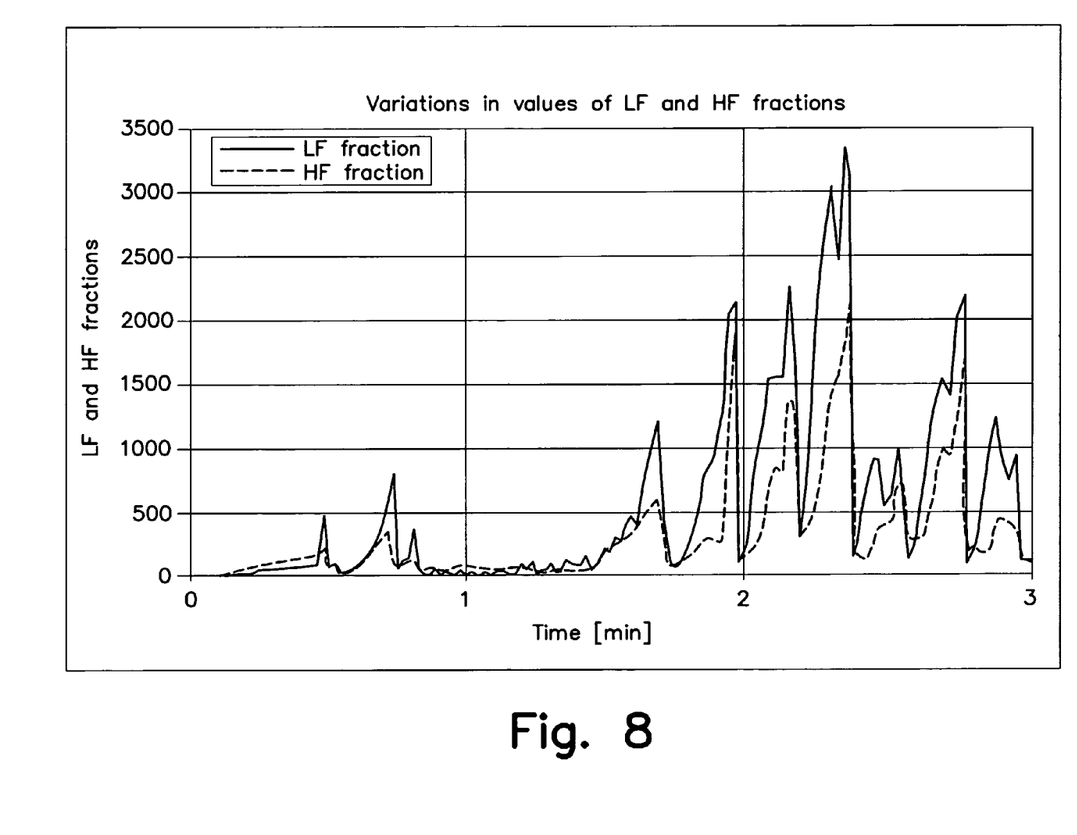
FIG. 8 shows variations in the measured values of the LF and HF fractions of a patient.

FIG. 8 shows variations in the measured values of the LF and HF fractions of the patient. It may clearly be seen that the variations in the LF and HF fractions follow a similar course. As already described LF/HF ratios are therefore basically well suited to determining the HRV since variations in the value of the LF fraction and the HF fraction can be compensated.

Figure 9:
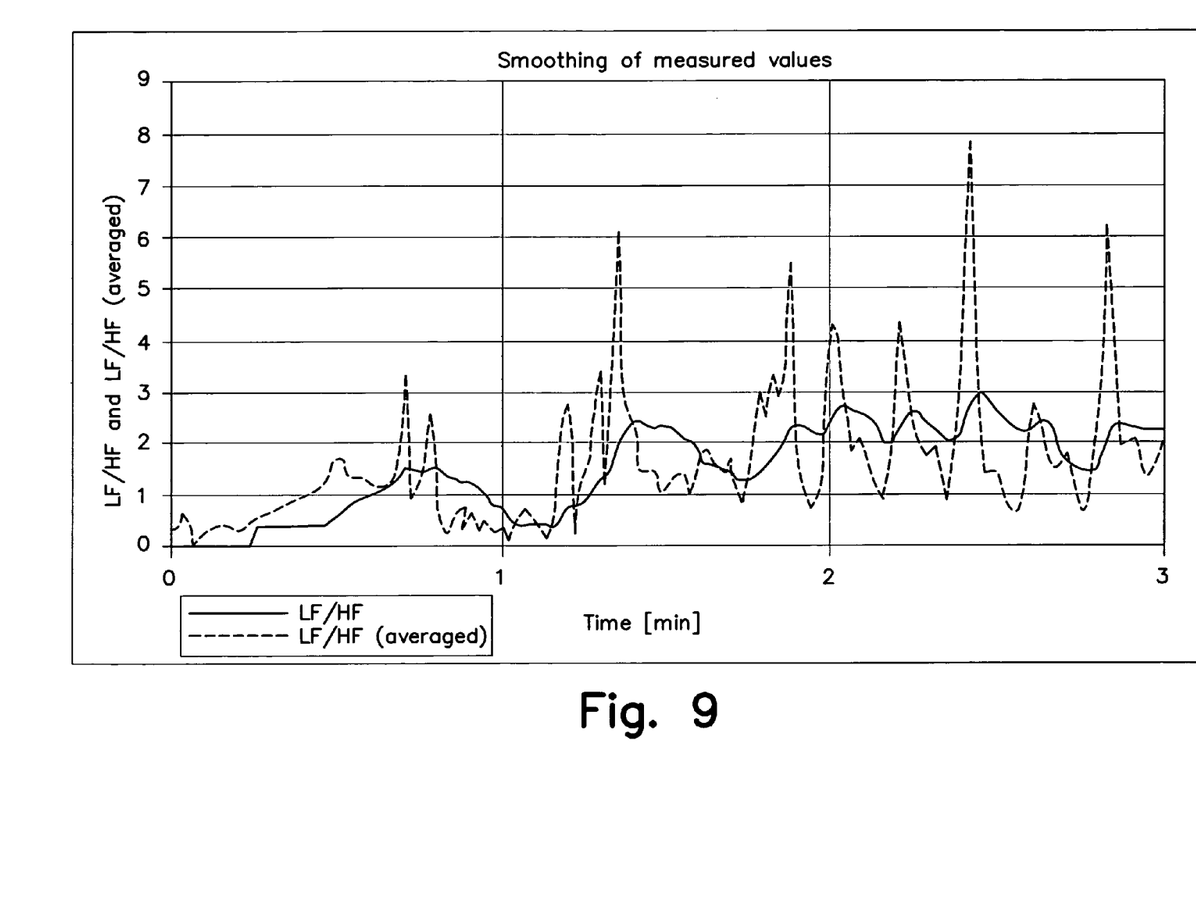
FIG. 9 shows the result of smoothing of the measured values used in evaluation, illustrated with the aid of the ratio LF/HF, FIG. 10a) shows the characteristic of the heart rate of a patient during a biofeedback session, FIG. 10b) shows the characteristic determined therefrom of parameters according to the invention and parameters known from the prior art for determining the HRV.
Figure 10:
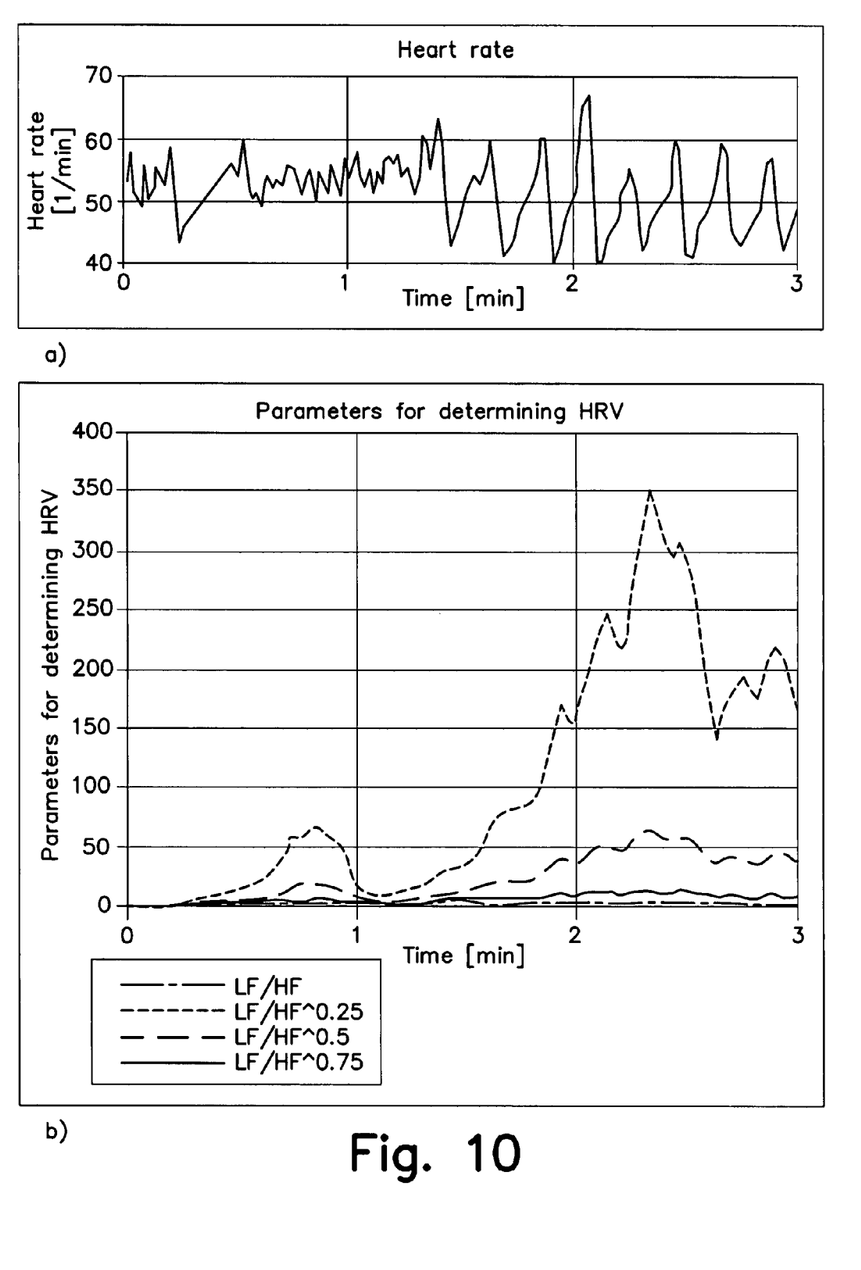

FIG. 9 shows the result of smoothing of the measured values used in evaluation, illustrated with the aid of the LF/HF ratio. In practice determination of an HRV parameter, for example according to the LF/HF ratio known from the prior art, in some cases leads to strongly oscillating curves as a function of time. These kinds of results can only be interpreted with difficulty, in particular with biofeedback training. To improve evaluation smoothing of the results is therefore carried out. In this case it is no longer the individual values that are illustrated but an average of, for example, the last ten values. Since this type of smoothing does not provide any results for the first nine values, smoothed curves accordingly only begin with the tenth value pair. FIG. 9 shows this kind of smoothing over the last 14 values using the LF/HF ratio as an example. Basically this method can be carried out for any result and will also be continually applied hereinafter.

FIG. 10a) shows the characteristic of the heart rate of a patient during a biofeedback session. This measured characteristic was used as the basis for the following evaluations. The transition from an irregular to a regular heart rate can be seen in the second minute. This transition identifies the occurrence of the RSA state.

FIG. 10b) shows the characteristic determined therefrom of parameters according to the invention and parameters known from the prior art for determining the HRV. The parameters known from the prior art correspond to the ratio LF/HF. The remaining three curves correspond to the HRV parameter $HRV_i = \tilde{I}_{max,i} * f(\tilde{I}_{ref,i})$ with the function according to the invention $$f(\tilde{I}_{ref}) = \frac{1}{(\tilde{I}_{ref})^a}$$

in each case where a=0.25, a=0.5 and a=0.75 and the proviso that $\tilde{I}_{ref}$ corresponds to the HF fraction and $\tilde{I}_{max}$ to the LF fraction.

It is clear that all three parameters according to the invention provide a greater function value than the LF/HF ratio, wherein the function value has a tendency to increase as the parameter a decreases. The evaluation also resulted in higher dynamics of the parameters according to the invention. The ratio of maximum to minimum value with the LF/HF ratio is therefore only 7.99. Corresponding values of 64.28, 31.72 and 16.32 result in the case of the parameters according to the invention with values a=0.25, a=0.5 and a=0.75. The dynamics therefore also have a tendency to increase as the parameter a decreases.

Figure 11:
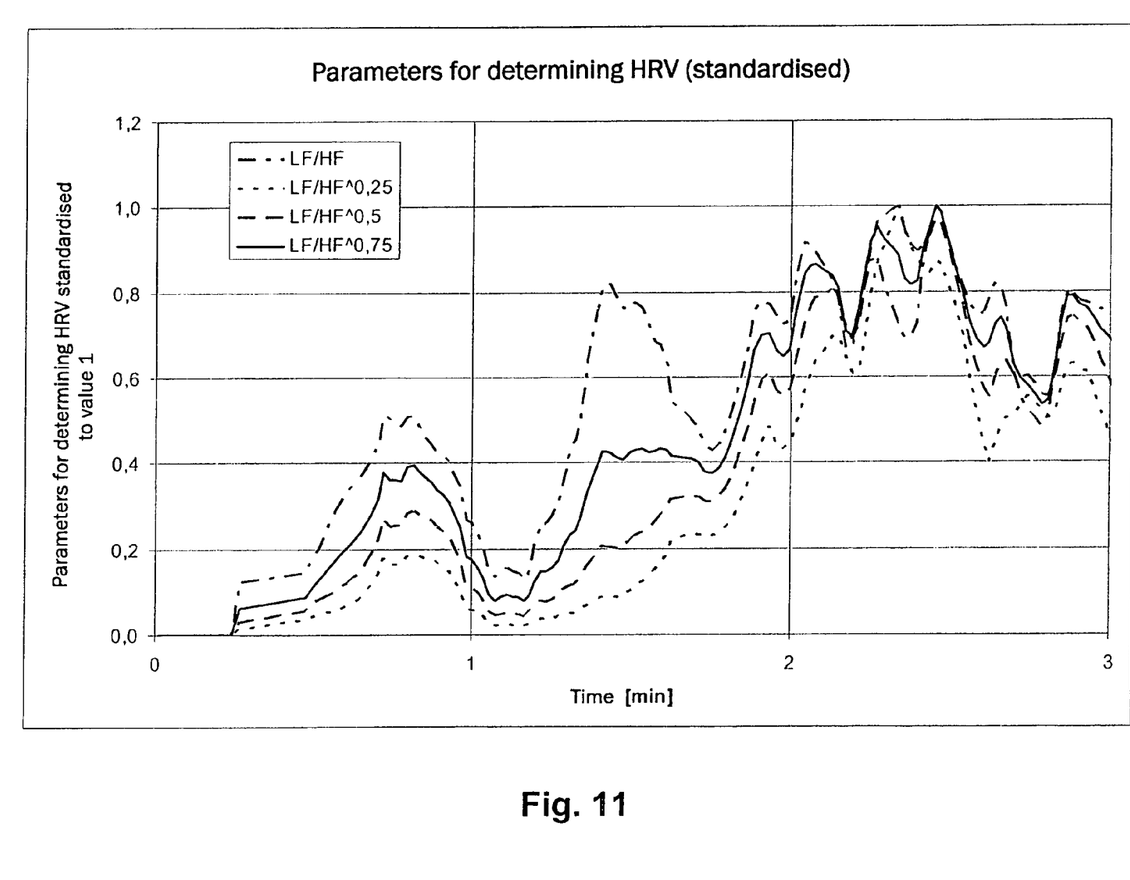
FIG. 11 shows the characteristic of parameters according to the invention and parameters known from the prior art for determining the HRV according to FIG. 10b), but in this instance standardized to the value 1.

FIG. 11 shows the characteristic of parameters according to the invention and parameters known from the prior art for determining the HRV according to FIG. 10b), but in this instance standardized to the value 1. The characteristics of all parameters within the first minute and within the third minute are qualitatively approximately the same. Clear differences can be seen in the characteristic in the second minute, however. These can be attributed to the different weighting of the HF effect.

Figure 12:
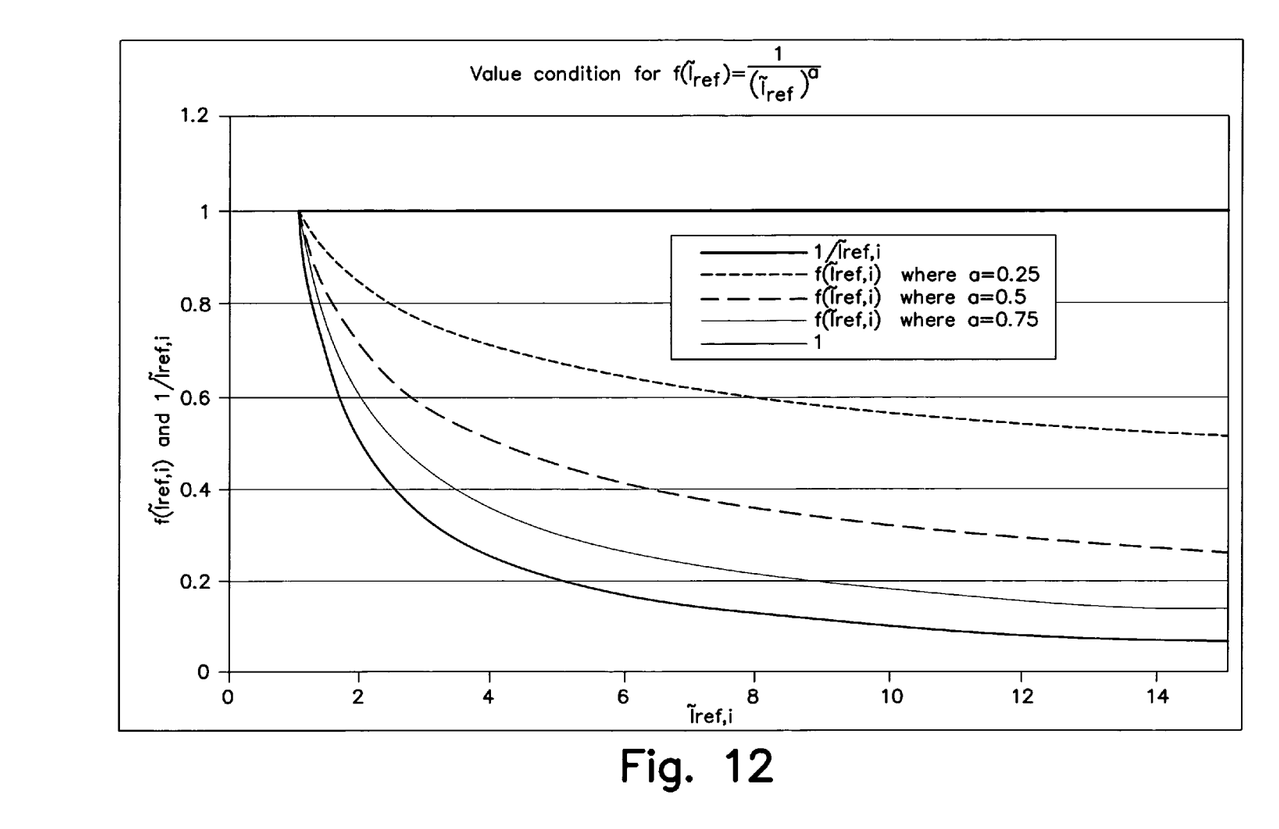

FIG. 12 shows the observance of the value condition for the function $$f(\tilde{I}_{ref}) = \frac{1}{(\tilde{I}_{ref})^a}$$

according to the invention used for evaluation with the values a=0.25, a=0.5 and a=0.75. The value condition is as follows $$1 > f(\tilde{I}_{ref,i}) > \frac{1}{\tilde{I}_{ref,i}}.$$

As FIG. 12 shows the term $f(\tilde{I}_{ref,i})$ is always less than one and always greater than the term $1/\tilde{I}_{ref,i}$. This result is also achieved for other values of the parameter a according to the invention, i.e. values between 0 and 1.

Figure 13:
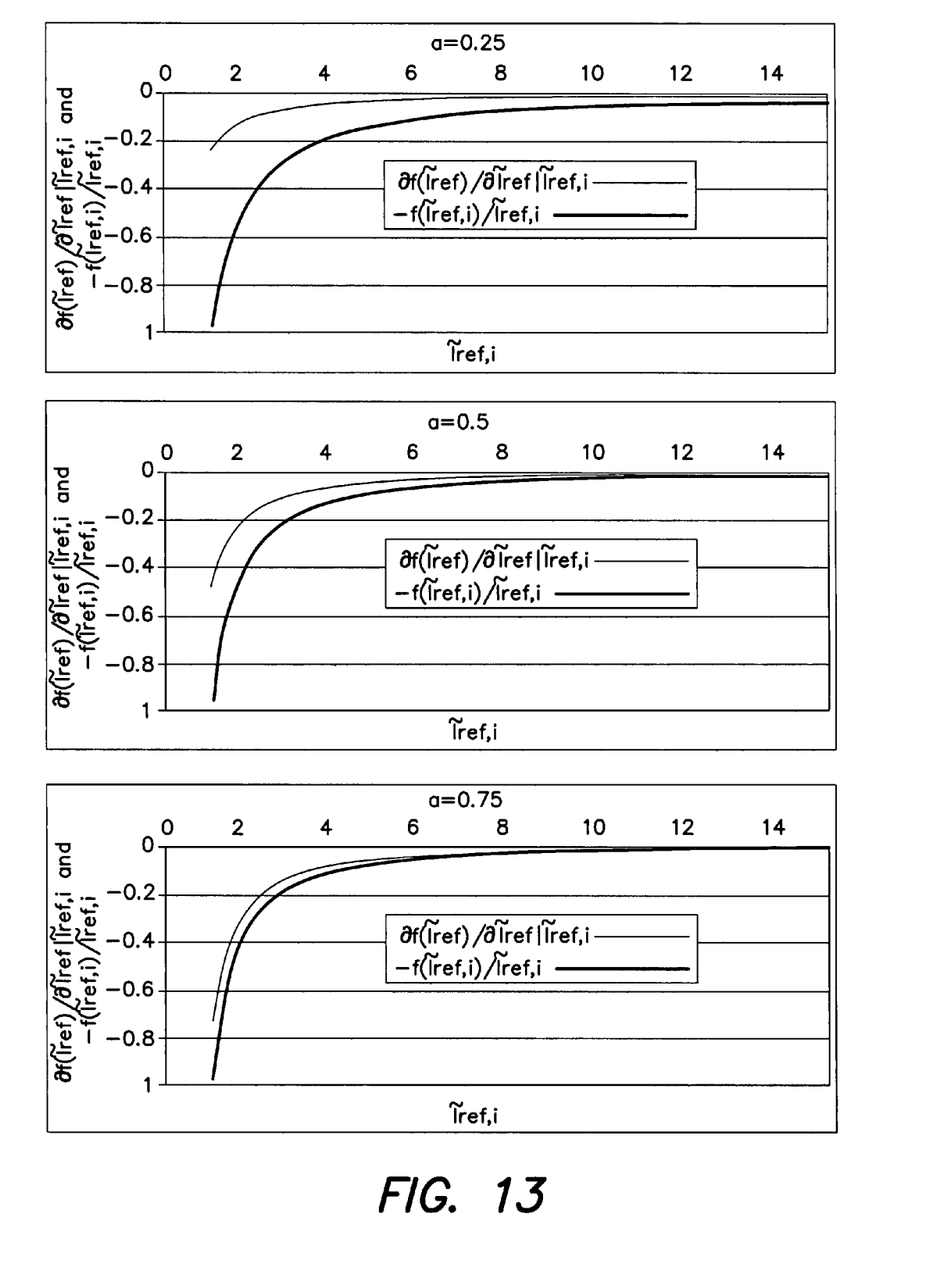

FIG. 13 shows the observance of the gradient condition for the function $$f(\tilde{I}_{ref}) = \frac{1}{(\tilde{I}_{ref})^a}$$

according to the invention used for evaluation with the values a=0.25, a=0.5 and a=0.75. The gradient condition is as follows $$0 > \frac{\partial f(\tilde{I}_{ref})}{\partial \tilde{I}_{ref}}\bigg|_{\tilde{I}_{ref,i}} > -\frac{f(\tilde{I}_{ref,i})}{\tilde{I}_{ref,i}}.$$

As FIG. 13 shows the term $$\frac{\partial f(\tilde{I}_{ref})}{\partial \tilde{I}_{ref}}\bigg|_{\tilde{I}_{ref,i}}$$

is always less than zero and always greater then the term $$-\frac{f(\tilde{I}_{ref,i})}{\tilde{I}_{ref,i}}.$$

This result is also achieved for other values of the parameter a according to the invention, i.e. values between 0 and 1.

The invention claimed is:

1. Method for online-displaying a HRV biofeedback signal to a patient with the following steps:
   providing a plurality of sampling sequences $f_{h,i}(kT_s)$ where $i=1, 2, 3, \ldots, m$ and $k=0, 1, 2, \ldots, n$, wherein each sampling sequence $f_{h,i}(kT_s)$ represents the sampling sequence of the heart rate $f_h$ of the patient over the period $n \cdot T_s$,
   determining a distribution function $F_{h,i}(f)$ for each sampling sequence $f_{h,i}(kT_s)$ as a function of frequency by means of a spectral analysis,
   determining a first integral fraction $I_{max,i}$ of the distribution function $F_{h,i}(f)$ for a first frequency range, wherein the first frequency range includes a maximum of the distribution function $F_{h,i}(f)$;
   determining a second integral fraction $I_{ref,i}$ of the distribution function $F_{h,i}(f)$ for a second frequency range which includes additional or different frequency ranges to the first frequency range,
   standardising the integral fractions $I_{max,i}$ and $I_{ref,i}$ using a standardising factor $K_{ref}$ where $$\tilde{I}_{max,i} = K_{ref} * I_{max,i}$$

and $$\tilde{I}_{ref,i} = K_{ref} * I_{ref,i}$$

in such a way that for the second integral fraction the condition $\tilde{I}_{ref,i} \geq 1$ is satisfied,
   determining a parameter $HRV_i$ for each sampling sequence $f_{h,i}(kT_s)$ with the respective integral fractions $\tilde{I}_{max,i}$ and $\tilde{I}_{ref,i}$ with a function $f(\tilde{I}_{ref})$ according to $$HRV_i = \tilde{I}_{max,i} * f(\tilde{I}_{ref,i}),$$

wherein the function $f(\tilde{I}_{ref})$ for each integral fraction $\tilde{I}_{ref,i}$ satisfies the conditions $$1 > f(\tilde{I}_{ref,i}) > \frac{1}{\tilde{I}_{ref,i}}$$

and $$0 > \frac{\partial f(\tilde{I}_{ref})}{\partial \tilde{I}_{ref}}\bigg|_{\tilde{I}_{ref,i}} > -\frac{f(\tilde{I}_{ref,i})}{\tilde{I}_{ref,i}}$$

and wherein the function $f(\tilde{I}_{ref})$, the first and second frequency ranges and the standardising factor $K_{ref}$ are the same for all m evaluated sampling sequences $f_{h,i}(kT_s)$, and
   using each parameter $HRV_i$ for the HRV biofeedback signal for online-displaying to the patient.

2. Method according to claim 1, wherein the function $f(\tilde{I}_{ref})$ is defined as follows:

$$f(\tilde{I}_{ref}) = \frac{1}{(\tilde{I}_{ref})^a} \text{ where } 0 < a < 1.$$

3. Method according to claim 2, wherein a=0.75.
4. Method according to claim 2, wherein a=0.5.
5. Method according to claim 2, wherein a=0.25.
6. Method according to claim 1, wherein the distribution function $F_{h,i}(f)$ is determined by way of a fast Fourier transform of the sampling sequence $f_{h,i}(kT_s)$.
7. Method according to claim 1, wherein the distribution function $F_{h,i}(f)$ is determined by way of an autoregressive spectral estimate of the sampling sequence $f_{h,i}(kT_s)$.

* * * * *